United States Patent
Kaneko et al.

(10) Patent No.: US 11,105,807 B2
(45) Date of Patent: Aug. 31, 2021

(54) METHOD FOR ESTIMATING PATHOLOGICAL TISSUE DIAGNOSIS RESULT (GLEASON SCORE) OF PROSTATE CANCER

(71) Applicant: KONICA MINOLTA, INC., Tokyo (JP)

(72) Inventors: Tomonori Kaneko, Hachioji (JP); Takatoshi Kaya, Inagi (JP)

(73) Assignee: KONICA MINOLTA, INC., Tokyo (JP)

( * ) Notice: Subject to any disclaimer, the term of this patent is extended or adjusted under 35 U.S.C. 154(b) by 22 days.

(21) Appl. No.: 15/761,637

(22) PCT Filed: Sep. 2, 2016

(86) PCT No.: PCT/JP2016/075771
§ 371 (c)(1),
(2) Date: Mar. 20, 2018

(87) PCT Pub. No.: WO2017/056844
PCT Pub. Date: Apr. 6, 2017

(65) Prior Publication Data
US 2018/0348223 A1    Dec. 6, 2018

(30) Foreign Application Priority Data
Sep. 28, 2015   (JP) .............................. JP2015-189611

(51) Int. Cl.
*G01N 33/574*    (2006.01)
*G01N 33/543*    (2006.01)
*G01N 33/53*     (2006.01)

(52) U.S. Cl.
CPC ....... *G01N 33/57434* (2013.01); *G01N 33/53* (2013.01); *G01N 33/543* (2013.01); *G01N 2440/38* (2013.01)

(58) Field of Classification Search
CPC ........... G01N 33/543; G01N 33/57434; G01N 33/53; G01N 2440/38
See application file for complete search history.

(56) References Cited

U.S. PATENT DOCUMENTS 9,285,368 B2 *   3/2016  Yamashita  ........... G01N 33/573
10,196,694 B2 *  2/2019  Yamashita  ........... G01N 33/573
(Continued)

FOREIGN PATENT DOCUMENTS

| JP | 6149624 A | 3/1986 |
| JP | 6149625 A | 3/1986 |

(Continued)

OTHER PUBLICATIONS

Fukushima et al. ("α1,2-Fucosylated and β-N-acetylgalactosaminylated prostate-specific antigen as an efficient marker of prostatic cancer", Glycobiology, vol. 20, No. 4, pp. 452-460, published Dec. 11, 2009) (Year: 2009).*

(Continued)

*Primary Examiner* — Tracy Vivlemore
*Assistant Examiner* — Nam P Nguyen
(74) *Attorney, Agent, or Firm* — Cantor Colburn LLP

(57) ABSTRACT

Provided is a method of obtaining an index value used for pathological tissue diagnosis of prostate cancer, which method has low invasiveness and can be performed at a low cost. The method is a method of estimating a Gleason score that represents the malignancy of prostate cancer, which method includes: measuring the content of a prostate-specific antigen having an N-acetylgalactosamine residue at a non-reducing terminal of a sugar chain in a sample; and estimating that the Gleason score is 7 or higher when the thus measured value is larger than a threshold value, or estimating that the Gleason score is 6 or lower when the measured value is smaller than a threshold value. The (Continued)

prostate-specific antigen is preferably quantified by a method including the step of binding a molecule having an affinity for β-N-acetylgalactosamine residue, such as *Wisteria floribunda* lectin, soybean agglutinin, *Vicia Villosa* lectin or an anti-β-N-acetylgalactosamine antibody, to the prostate-specific antigen.

4 Claims, 5 Drawing Sheets

(56) References Cited

U.S. PATENT DOCUMENTS

| | | | |
|---|---|---|---|
| 2005/0221397 A1* | 10/2005 | Saito | G01N 33/57434 435/7.23 |
| 2009/0023220 A1 | 1/2009 | Amano et al. | |
| 2011/0294141 A1 | 1/2011 | Yamashita et al. | |
| 2011/0236995 A1 | 9/2011 | Hirano et al. | |
| 2015/0140571 A1* | 5/2015 | Kaneko | G01N 33/566 435/7.1 |
| 2019/0383818 A1* | 12/2019 | Kaneko | G01N 21/553 |

FOREIGN PATENT DOCUMENTS

| | | |
|---|---|---|
| JP | S61205863 A | 9/1986 |
| JP | H07270415 A | 10/1995 |
| JP | H07270416 A | 10/1995 |
| JP | 2000053590 A | 2/2000 |
| JP | 3731891 B2 | 10/2005 |
| JP | 2011137754 A | 7/2011 |
| JP | 2013076666 A | 4/2013 |
| JP | 5313509 B2 | 10/2013 |
| JP | 2014174018 A | 9/2014 |
| WO | 2009008381 A2 | 1/2009 |
| WO | 2010064683 A1 | 6/2010 |
| WO | 2010090264 A1 | 8/2010 |
| WO | 2012029342 A1 | 3/2012 |
| WO | WO2013161614 A1 * | 10/2013 |

OTHER PUBLICATIONS

International Search Report corresponding to Application No. PCT/JP2016/075771; dated Nov. 15, 2016.
Tobisawa Yuki, Serum LACDINAC-PSA Determined by Surface Plasmon Field-Enhanced Fluorescence Spectroscopy (SPFS)-Based Assay System has Improved Diagnostic Accuracy Than PSA, Journal of Urology, Apr. 2016, vol. 195, No. 4S, Suppl., p. E15-E16.
Tomonori Kaneko, "Development of a Prostate Cancer Diagnostic System Based on Surface Plasmon Field-Enhanced Fluorescence Spectroscopy", Konica Minolta Technol Rep, Jan. 2016, vol. 13, pp. 73-78.
Written Opinion of the International Searching Authority corresponding to Application No. PCT/JP2016/075771; dated Nov. 15, 2016.
JPO Notification of Reasons for Refusal corresponding to Application No. 2017-543048; dated Nov. 19, 2019.
Fukushima et al., "α1,2-Fucosylated and β-N-acetylgalactosaminylated prostate-specific antigen as an efficient marker of prostatic cancer", Glycobiology, 2010, vol. 20, No. 4, pp. 452-460, Advance Access Publication on Dec. 11, 2009.
JPO Notice of Reasons of Refusal corresponding to JP2017-543048 dated Mar. 10, 2020.

* cited by examiner

METHOD FOR ESTIMATING PATHOLOGICAL TISSUE DIAGNOSIS RESULT (GLEASON SCORE) OF PROSTATE CANCER

CROSS REFERENCE TO RELATED APPLICATIONS

This is the U.S. national stage of application No. PCT/JP2016/075771, filed on Sep. 2, 2016. Priority under 35 U.S.C. § 119(a) and 35 U.S.C. § 365(b) is claimed from Japanese Application No. 2015-189611, filed on Sep. 28, 2015, the disclosure of which is also incorporated herein by reference.

TECHNICAL FIELD

The present invention relates to a method of estimating a pathological tissue diagnosis result pertaining to the malignancy of prostate cancer, which is known as Gleason score.

BACKGROUND ART

Prostate cancer primarily occurs in men over 60 years of age, and in Western countries, prostate cancer is the second leading cause of cancer-related death in men after lung cancer. For determination of a prostate cancer therapeutic strategy, the progress (stage) and malignancy of the cancer serve as important indices. Of these indices, the malignancy of prostate cancer has a broad distribution that ranges from a state where hardly any proliferation is observed and follow-up without treatment is possible to a state where the cancer has metastasized to bones and lymph nodes, and has caused exacerbation showing resistance to hormone antagonists. Therefore, it is desired to accurately judge the malignancy of prostate cancer.

As a classification that indicates the malignancy of prostate cancer, "Gleason score" which represents a diagnostic result of a cancer pathological tissue as a score has been widely used. Prostate cancer tissues can be classified into 5 stages of Grade 1 to Grade 5 based on the morphology and the mode of infiltrative growth (Gleason grading system). A Gleason score is a total value of a grade given to an image of a tissue occupying the largest area based on the Gleason grading system and a grade given to an image of a tissue occupying the second largest area, which images are obtained by observation of a certain pathological tissue under a microscope (these two grades are the same in some cases). Generally, it is considered that a Gleason score of 2 to 6 indicates low malignancy, a Gleason score of 7 indicates moderate malignancy, and a Gleason score of 8 to 10 indicates high malignancy; therefore, whether or not the Gleason score is 7 or higher serves as a principal criterion.

However, in order to perform such pathological tissue diagnosis, it is necessary to collect a prostate tissue by inserting needles (a total of 8 or more needles) through rectum (needle biopsy). Needle biopsy also has drawbacks in that not only it is highly invasive and expensive for patients but also a diagnosis cannot be made when the needles do not reach the prostate cancer tissue.

Meanwhile, for prostate-related diseases such as prostate cancer and prostatic hyperplasia, studies are being made with a focus on their relationships with a prostate-specific antigen (PSA) having a specific sugar chain that exists in samples (e.g., blood) of patients. Conventionally, methods of diagnosing whether or not a patient has prostate cancer by quantifying all PSAs (total PSA) contained in a sample and comparing the thus obtained value with a threshold value, or by quantifying free PSA not binding with a1-antichymotrypsin and comparing the ratio of the amount of the free PSA with respect to the amount of all PSAs (free PSA/total PSA ratio) with a threshold value, have been known. However, in recent years, it has been gradually elucidated that, depending on the disease affecting the patient, the properties of the sugar chains of PSAs vary, in other words, the amount (ratio) of a PSA having a specific sugar chain varies; therefore, several proposals have been made on methods that utilize this finding to diagnose whether or not a patient has prostate cancer or prostatic hyperplasia.

For example, Patent Document 1 (WO 2009/008381) discloses a method in which a PSA having a fucose-unbound sugar chain and a PSA having a fucose-bound sugar chain that are contained in a sample derived from a subject are analyzed by mass spectrometry and the subject is identified to have prostate cancer when the amount of the latter is greater than that of the former (the ratio of the signal intensity of the latter with respect to the signal intensity of the former is higher than 1.0), or the subject is identified to have benign prostatic hyperplasia otherwise.

Patent Document 2 (WO 2010/064683) discloses a method in which the amount of a sugar chain having LacdiNAc (N-acetylgalactosamine-N-acetylglucosamine) and that of a sugar chain having LacNAc (galactose-N-acetylglucosamine) but not LacdiNAc are quantified for a PSA contained in a sample derived from a subject and the subject is determined to have prostate cancer when the amount of the former is greater than 30% of the amount of the latter.

Patent Document 3 (JP 2011-137754A) discloses a method in which the sugar chain structure of a PSA contained in a sample derived from a subject is analyzed and the subject is determined to have prostate cancer when three or more sugar chains having LacdiNAc exist.

Patent Document 4 (WO 2010/090264) discloses a method in which a PSA having a β-N-acetylgalactosamine residue and/or a PSA having a fucose α(1,2) galactose residue is/are quantified in a sample (e.g., serum) derived from a patient and the patient is determined to have prostate cancer when the absolute amount thereof and/or the ratio thereof with respect to total PSA is larger than a prescribed cut-off value, or the patient is determined to have prostatic hyperplasia otherwise. It is described that the PSA having a β-N-acetylgalactosamine residue can be quantified using a lectin having an affinity for this residue, such as TJA-II (*Trichosanthes japonica* agglutinin-II: *Trichosanthes japonica* lectin-II) or WFA (*Wisteria floribunda* agglutinin: *Wisteria floribunda* lectin) and that the PSA having a fucose α(1,2) galactose residue can be quantified using a lectin having an affinity for this residue, such as UEA-I (*Ulex europaeus* agglutinin-I: *Ulex europaeus* lectin-I) or TJA-II. It is also described that the above-described PSAs having the respective prescribed residues can each be quantified through adsorption and elution thereof, for example, using a column in which a lectin is bound to a carrier (lectin affinity column).

Moreover, Patent Document 5 (JP 2013-076666A) discloses a method of quantifying a PSA having the same specific residue(s) as in Patent Document 4 by a sandwich assay, such as SPFS (Surface Plasmon-Field Enhanced Fluorescence Spectroscopy), using a solid-phase primary antibody for the PSA and a secondary capturing molecule obtained by labeling a lectin having a high affinity for the residue(s) of the PSA with a fluorescent dye.

However, none of these Patent Documents 1 to 5 describe a correlation between each method disclosed therein and the malignancy of prostate cancer, such as Gleason score. Particularly, in Example 1 of Patent Document 4, while PSAs having the above-described respective specific sugar chains were quantified using TJA-II and it was shown that prostatic hyperplasia patients and prostate cancer patients can be distinguished from each other, it was analyzed that no significant difference was found in terms of the Gleason score. Further, in Example 2 of Patent Document 4, PSAs having the above-described respective specific sugar chains were quantified using WFA and it was analyzed that, for example, WFA showed the same tendency as TJA-II (the WFA binding rate was slightly lower but substantially correlates with that of TJA-II) and there is possibly a PSA having only a fucose α(1,2) galactose residue without a β-N-acetylgalactosamine residue; however, the quantification was performed only for three samples derived from prostate cancer patients, and no analysis was made with regard to the Gleason score. In Patent Document 4, TJA-II and WFA are both exemplified as lectins having an affinity for β-N-acetylgalactosamine residue bound to a non-reducing terminal (terminal on the opposite side of a reducing terminal bound to a protein) of a sugar chain (see [0020]); however, these lectins are different in terms of their affinity for other residues. That is, TJA-II is a lectin that shows a strong affinity for both β-N-acetylgalactosamine residues (GalNAcβ1→R; R represents other residue of a sugar chain or an amino acid residue of a protein) and fucose α(1,2) galactose residues (Fucα1→2Galβ1→R) (see [0022]). Meanwhile, WFA shows a strong affinity for β-N-acetylgalactosamine residues (GalNAcβ1→R), such as GalNAc (β1→4)Gal residue and GalNAc(β1→4)GlcNAc residue, but WFA doesn't show the affinity for fucose α(1,2) galactose residues (Fucα1→2Galβ1→R) (see [0023]).

RELATED ART DOCUMENTS

Patent Documents

[Patent Document 1] WO 2009/008381
[Patent Document 2] WO 2010/064683
[Patent Document 3] JP 2011-137754A
[Patent Document 4] WO 2010/090264
[Patent Document 5] JP 2013-076666A

SUMMARY

Problems to be Solved by the Invention

As described above, conventional pathological tissue diagnosis that requires needle biopsy imposes a heavy burden on patients. Patients would be greatly benefited if a pathological tissue diagnosis result of prostate cancer, such as a Gleason score representing the malignancy of prostate cancer, could be obtained by a method that has low invasiveness and low cost as in the case of a blood test.

An objective of the present invention is to provide a method of obtaining an index value used for pathological tissue diagnosis of prostate cancer, which method has low invasiveness and can be performed at a low cost.

Technical Solution

The present inventors discovered that among samples prepared from blood which contained PSAs, with regard to a PSA that can be quantified through binding with WFA, that is, a content of "PSA having an affinity for WFA", there is a statistically significant difference in terms of the content thereof between a sample group derived from prostate cancer patients having a Gleason score of 7 or higher and other sample groups as well as between a sample group derived from prostate cancer patients having a Gleason score of 6 or lower and other sample groups; and that, by setting an appropriate threshold value, whether the Gleason score is 7 or higher, or 6 or lower can be estimated with high accuracy.

As already described in Patent Document 4, the content of "PSA having an affinity for TJA-II" does not correlate with Gleason scores and thus cannot be used for performing the above-described discrimination of Gleason scores. It is speculated that such a difference in whether or not a discrimination can be made is attributed to a difference in sugar chain recognition between WFA and TJA-II, that is, a difference that PSAs binding with WFA only include PSAs having a β-N-acetylgalactosamine residue and do not include PSAs having a fucose α(1,2) galactose residue while PSAs binding with TJA-II include both PSAs having a fucose α(1,2) galactose residue and PSAs having a β-N-acetylgalactosamine residue.

Further, the present inventors also discovered that it is possible to perform the same determination even when the quantification of "PSA having an affinity for WFA" is expanded and generalized as described above and not only a PSA having a β-N-acetylgalactosamine residue but also a PSA having an α-N-acetylgalactosamine residue (the abundance of such a PSA is believed to be low based on the structural analysis results of the PSA sugar chain obtained by mass spectrometry) are included in the quantification subjects, in other words, the PSAs to be the quantification subjects include not just the PSAs having an affinity for WFA and can be defined as PSAs having an N-acetylgalactosamine residue at a non-reducing terminal of a sugar chain.

The present invention made on the basis of these findings provides, in one aspect, "a method of estimating a Gleason score that represents the malignancy of prostate cancer, the method comprising: measuring the content of a PSA having an N-acetylgalactosamine residue at a non-reducing terminal of a sugar chain in a sample; and estimating that the Gleason score is 7 or higher when the thus measured value is larger than a threshold value, or estimating that the Gleason score is 6 or lower when the measured value is smaller than a threshold value.

In other words, one aspect of the present invention provides "a method of measuring the content of a PSA having an N-acetylgalactosamine residue at a non-reducing terminal of a sugar chain in a sample, the method comprising at least the step of binding a molecule having an affinity for an N-acetylgalactosamine residue to the PSA". This measurement method can be utilized for estimating a Gleason score that represents the malignancy of prostate cancer, and the Gleason score can be estimated to be 7 or higher when the thus measured value is larger than a threshold value, or the Gleason score can be estimated to be 6 or lower when the measured value is smaller than a threshold value.

It is noted here that the threshold value for estimating the Gleason score to be 7 or higher and the threshold value for estimating the Gleason score to be 6 or lower, which are used in the present invention, are different from those threshold values used for a different purpose in prior art, such as the threshold value used for judging between prostate cancer and prostatic hyperplasia as described in Patent Document 4. From this standpoint, the present invention can be distinguished from prior art.

Advantageous Effects of the Invention

The present invention enables to estimate the malignancy of prostate cancer which has a diagnostically important meaning, that is, whether or not the Gleason score is 7 or higher, or 6 or lower, with a desired accuracy, not by a test that imposes a heavy burden on patients as in needle biopsy but by a test that has low invasiveness and can be performed at a low cost as in a blood test. Consequently, necessary treatments can be performed and follow-ups can be made for prostate cancer patients while maintaining their QOL.

BRIEF DESCRIPTION OF THE DRAWINGS

FIG. 1 provides schematic drawings that illustrate reactions taking place in a measurement region 38 inside a flow channel 36 during quantification of a GalNAc-PSA 100 contained in a sample using an SPFS measuring member 16, wherein

FIG. 2 provides schematic drawings that illustrate general embodiments of an SPFS system 1, wherein

MODE FOR CARRYING OUT THE INVENTION

Figure 1A:
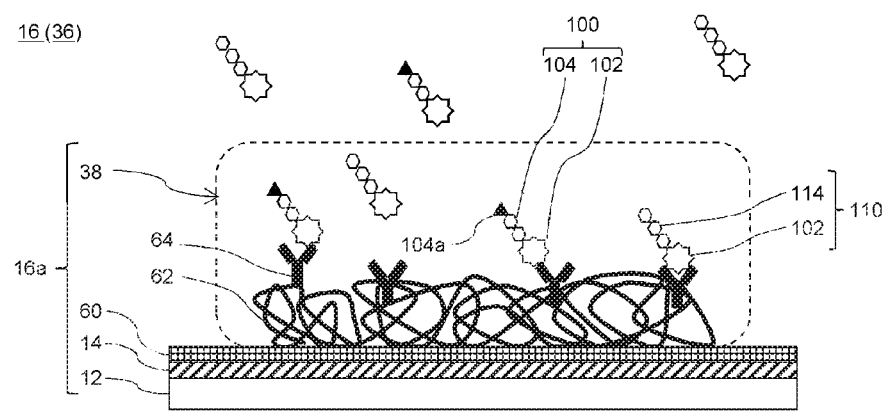
FIG. 1A illustrates reactions in the capturing step performed for binding the GalNAc-PSA 100 to an anti-PSA antibody 64 carried on a support 62.

In the present specification, the following terms may each be abbreviated as follows. That is, the term "PSA having an N-acetylgalactosamine residue at a non-reducing terminal of a sugar chain" may be referred to as "GalNAc-PSA". The term "molecule having an affinity for an N-acetylgalactosamine residue" may be referred to as "GalNAc residue-affinity molecule". The terms "N-acetylgalactosamine residue" and "β-N-acetylgalactosamine residue" may be referred to as "GalNAc residue" and "β-GalNAc residue", respectively, and the terms "molecule/lectin having an affinity for an N-acetylgalactosamine residue" and "molecule/lectin having an affinity for aβ-N-acetylgalactosamine residue" may be referred to as "GalNAc residue-affinity molecule/lectin" and "β-GalNAc residue-affinity molecule/lectin", respectively.

In the method of estimating a Gleason score according to the present invention, the content of a PSA having an N-acetylgalactosamine residue at a non-reducing terminal of a sugar chain (GalNAc-PSA) in a sample is measured, and the Gleason score is estimated to be 7 or higher when the measured value is larger than a threshold value, or the Gleason score is estimated to be 6 or lower when the measured value is smaller than a threshold value.

The term "sample" refers to a material for the measurement of the GalNAc-PSA content, which material is collected from a subject to which the method of estimating a Gleason score according to the present invention is applied, and examples of the sample include liquid samples that can be collected by a non-invasive or low-invasive method, such as blood, urea and peritoneal fluid. For example, a sample prepared from an anticoagulated whole blood, preferably serum or plasma, is suitable as the sample used in the present invention. Depending on the GalNAc-PSA quantification method, as required, the sample may be prepared with an addition of a diluent, a reagent or the like.

The subject to which the method of estimating a Gleason score according to the present invention is applied, namely the subject from which a sample is collected, is typically a human; however, the subject may be a non-human mammalian animal, such as a model animal of a human disease. Examples of a human subject typically include patients who have been definitively diagnosed with prostate cancer and individuals possibly having prostate cancer, for whom it is necessary to know the malignancy of prostate cancer, and examples of a non-human mammalian animal subject include model animals such as mice and rats, in which prostate cancer has been induced.

[Quantification Method]

A method for measuring the GalNAc-PSA content in a sample is not particularly restricted as long as the method can yield a measured value with such an accuracy that allows comparison of the measured value with a prescribed threshold value, and a variety of quantification methods can be employed.

As a GalNAc-PSA quantification method, a method which can be carried out by a relatively simple means and comprises the step of binding a molecule having an affinity for an N-acetylgalactosamine residue (GalNAc residue-affinity molecule) to a GalNAc-PSA is preferred; however, other method such as a mass spectrometry-based method can be employed as well.

GalNAc Residue-Affinity Molecule

The GalNAc residue-affinity molecule is preferably a molecule having an affinity for aβ-N-acetylgalactosamine residue (β-GalNAc residue-affinity molecule). As the GalNAc residue-affinity molecule, a lectin having an affinity for GalNAc residue (GalNAc residue-affinity lectin) or an antibody whose epitope is GalNAc residue (anti-GalNAc antibody) can be used.

Similarly, as the β-GalNAc residue-affinity molecule, a lectin having an affinity for β-GalNAc residue (β-GalNAc residue-affinity lectin) or an antibody whose epitope is β-GalNAc residue (anti-β-GalNAc antibody) can be used. For the matters described below, the term "GalNAc residue" is interchangeable with the term "β-GalNAc residue" as appropriate.

GalNAc Residue-Affinity Lectin

A lectin is a protein having an affinity for a specific sugar residue, that is, a protein that recognizes and binds to a specific sugar residue, and a large variety of lectins (also referred to as "agglutinins") derived from various organisms are known. The sugar residue for which a lectin has an affinity varies depending on the type of the lectin, and many lectins have an affinity not just for one sugar residue but for plural sugar residues (however, the affinity for a specific sugar residue is strong and that for other sugar residues is weak). Generally speaking, while antibodies whose epitope is a specific sugar residue in a sugar chain, such as an anti-GalNAc antibody, are difficult to prepare, GalNAc residue-affinity lectins not only are inexpensive and available in a large amount but also have excellent stability and can be stored over a long time; therefore, GalNAc residue-affinity lectins are preferred as GalNAc residue-affinity molecules.

Various GalNAc residue-affinity lectins have been known, and it is also possible that a GalNAc residue-affinity lectin will be newly isolated from a different organism. In the present invention, any lectin can be used as long as it has a sufficiently strong affinity for GalNAc residue, that is, the lectin has no affinity for other sugar residues, or the lectin has an affinity for other sugar residues as well but the affinity for other sugar residues is sufficiently weaker than the affinity for GalNAc residue (e.g., the binding constant is lower by several orders), and a GalNAc-PSA can be quantified with sufficient accuracy.

Specific examples of GalNAc residue-affinity lectins, preferably β-GalNAc residue-affinity lectins, include *Wisteria floribunda* lectin (*Wisteria floribunda* agglutinin: WFA), soybean agglutinin (SBA), and *Vicia Villosa* lectin (VVL). These lectins can be separated (extracted) and purified from the organisms (e.g., seeds) from which the lectins are each derived, or can be obtained as commercially available products.

WFA is sometimes denoted as "WFL" (*Wisteria floribunda* lectin) and is a lectin (agglutinin) derived from *Wisteria floribunda*. WFA has an affinity for N-acetyl-D-galactosamine residues (GalNAc), that is, for both α-N-acetyl-D-galactosamine residue (α-GalNAc) and β-N-acetyl-D-galactosamine residue (β-GalNAc), and is capable of binding to, for example, GalNAc(α1→6)Gal residue, GalNAc(α1→3)Gal/GalNAc residue, GalNAc(β1→4)Gal residue and GalNAc(β1→4)GlcNAc residue, which are positioned at a non-reducing terminal of a sugar chain, as well as GalNAc-Ser/Thr (serine or threonine) and the like that are positioned at a reducing terminal of a sugar chain. In addition, WFA has a relatively weak affinity for lactose and galactose.

SBA is a lectin (agglutinin) derived from soybean. SBA also has an affinity for N-acetyl-D-galactosamine residues (GalNAc), that is, for both α-N-acetyl-D-galactosamine residue (α-GalNAc) and β-N-acetyl-D-galactosamine residue (β-GalNAc); however, the affinity for the former is slightly stronger than the affinity for the latter. SBA is capable of binding to, for example, GalNAc(α1→3)Gal residue, GalNAc(β1→4)Gal residue and GalNAc(β1→4) GlcNAc residue, which are positioned at a non-reducing terminal of a sugar chain, and has a relatively weak affinity for galactose as well.

VVL is sometimes denoted as "VVA" (*Vicia villosa* agglutinin) and is a lectin (agglutinin) derived from hairy vetch (*Vicia villosa*). VVL also has an affinity for N-acetyl-D-galactosamine residues (GalNAc), that is, for both α-N-acetyl-D-galactosamine residue (α-GalNAc) and β-N-acetyl-D-galactosamine residue (β-GalNAc), and is capable of binding to, for example, GalNAc(α1→3)Gal residue, GalNAc(β1→4)Gal residue and GalNAc(β1→4)GlcNAc residue, which are positioned at a non-reducing terminal of a sugar chain.

Embodiments of GalNAc-PSA Quantification Method

A representative embodiment (first embodiment) of the GalNAc-PSA quantification method comprising the step of binding a GalNAc residue-affinity molecule to a GalNAc-PSA is, for example, a method which comprises allowing a GalNAc residue-affinity molecule along with a molecule specifically binding to other PSA to bind to a GalNAc-PSA and thereby forming a sandwich-type complex composed of these three molecules. Specific examples of this sandwich-type complex include sandwich-type complexes composed of an anti-PSA antibody whose epitope is a PSA protein carried (immobilized) on a support, a GalNAc-PSA and a fluorescently-labeled GalNAc-affinity lectin or anti-GalNAc antibody.

The "anti-PSA antibody" can be prepared by a commonly used method, or it can be purchased as a commercial product. From the standpoint of the measurement stability, a monoclonal antibody is used more preferably than a polyclonal antibody. Further, in order not to prevent a fluorescently-labeled lectin from recognizing and binding to a specific sugar residue (GalNAc in the present invention) in a sugar chain, it is preferred to use an antibody whose epitope is a protein moiety, not a sugar chain, of PSA. As such anti-PSA monoclonal antibodies whose epitope is a PSA protein, for example, clones such as PS2, PS3, PS4, PS5, PS6, PS15, 2H9, 3B4, 5A6, 5G6, 8G4, 9A8, 9G2, PS1, 8A6, 2H9, 1H12 and No. 79 are known and commercially available. The anti-GalNAc antibody, preferably an anti-β-GalNAc antibody, can also be prepared in the same manner and, for example, clones such as 100-2H5-A, 114-2H12-C, 259-2A1, 273-3F2, 99-2A5-B and SMLDN1.1 are known.

The fluorescently-labeled GalNAc-affinity lectin can be prepared by binding a desired fluorescent substance to the above-described GalNAc-affinity lectin in accordance with a commonly used method and, in this process, a commercially available fluorescent substance labeling kit or the like can be used as well. The fluorescent substance is not particularly restricted and, for example, a fluorescent dye capable of emitting an appropriate fluorescence in SPFS can be used. The fluorescently-labeled anti-GalNAc antibody can also be prepared in the same manner.

As a method of quantifying the amount of the thus formed sandwich-type complex containing the GalNAc residue-affinity molecule as described above, that is, the GalNAc-PSA content in a sample, SPFS (Surface Plasmon-Field Enhanced Fluorescence Spectroscopy), which is known as a method capable of quantifying a measurement subject with high sensitivity and high accuracy, is preferred. The GalNAc-PSA contained in a sample can be quantified based on the intensity of fluorescence emitted from the fluorescent substance contained in the sandwich-type complex, which is measured by SPFS.

Another embodiment (second embodiment) of the GalNAc-PSA quantification method comprising the step of binding a GalNAc residue-affinity molecule to a GalNAc-PSA includes a method which utilizes a column loaded with a carrier bound with a lectin having an affinity for the GalNAc residue (lectin affinity column). That is, a sample is applied to the lectin affinity column to bind the GalNAc-PSA to the lectin and, subsequently, a hapten sugar-containing elution buffer is applied thereto to dissociate the GalNAc-PSA and a fraction containing the GalNAc-PSA is recovered, after which the GalNAc-PSA content in the fraction can be measured by immunoassay. In the second embodiment, for the quantification of GalNAc-PSA in the GalNAc-PSA-containing fraction, since substantially all of the PSAs contained in the fraction have the GalNAc residue, it is not required to use a labeled GalNAc residue-affinity molecule (lectin), and a labeled anti-PSA antibody whose epitope is a PSA protein can be used. The GalNAc-PSA in the GalNAc-PSA-containing fraction can be quantified by, for example, a chemiluminescent enzyme immunoassay in which an immunocomplex composed of an anti-PSA antibody-bound magnetic particle, a PSA and an alkaline phosphatase-labeled anti-PSA antibody is formed and the emission intensity is subsequently measured with an addition of a chemiluminescent substrate, or by SPFS method in which an immunocomplex composed of an immobilized anti-PSA antibody, a PSA and a fluorescently-labeled anti-PSA antibody is formed and the fluorescence intensity is subsequently measured by SPFS.

SPFS Measurement Method

SPFS is a method which utilizes a phenomenon that, when a metal thin film formed on the upper surface of a dielectric member is irradiated with an incoming light from the back side (the side in contact with the dielectric member) at an angle that causes attenuated total reflection (ATR), an evanescent wave generated on the surface (the side on which a measurement region is formed) by the incoming light transmitting through the metal thin film is enhanced by several ten times to several hundred times due to resonance with surface plasmon, and uses the thus enhanced evanescent wave as an excitation light so as to efficiently allow a fluorescent substance labeling a subject to be measured that is captured in the measurement region to emit fluorescence. The subject to be measured in a sample can be quantified by measuring the intensity of the fluorescence, and the measured value of the sample is compared with a fluorescence intensity value measured for a standard sample having a known concentration, whereby the measured value can be converted into the content (concentration) of the subject to be measured in the sample. SPFS performed in this manner is extremely sensitive as compared to conventional fluorescent labeling methods such as ELISA; therefore, it is preferred as a quantification method used in those cases where the concentration of the subject to be measured in a sample at an extremely low.

In the present invention, the Gleason score is estimated based on the content (concentration) of a GalNAc-PSA in a sample; however, it is also possible to, for an analysis, directly use a "measured value" obtained by a quantification method such as SPFS in accordance with a prescribed measurement protocol without converting the "measured value" into "concentration" expressed in a prescribed unit such as ng/mL or U (unit)/mL. For example, in SPFS, measured values of fluorescence intensity are usually expressed in an arbitrary unit (a.u.). A threshold value in this arbitrary unit may be set based on the measured values expressed in the arbitrary unit that are obtained for samples under the same condition, and the Gleason score may be estimated from the measured value of each sample obtained under the same condition.

A general embodiment in which a sandwich-type complex composed of an anti-PSA antibody, a GalNAc-PSA and a fluorescently-labeled GalNAc residue-affinity molecule is formed and the intensity of fluorescence emitted from this complex (fluorescent substance) is subsequently measured by SPFS will now be described referring to FIG. 1.

Figure 1B:
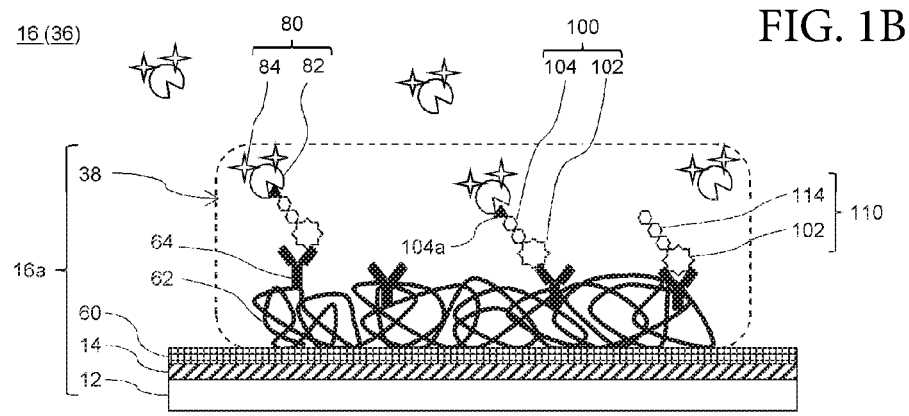
FIG. 1B illustrates reactions in the labeling step performed for binding a fluorescently-labeled GalNAc-affinity molecule 80 to the GalNAc-PSA 100 captured on the anti-PSA antibody 64.

The steps performed in SPFS can be broadly divided into the steps of "pre-measurement stage" and the steps of "measurement stage". The steps of the pre-measurement stage are the steps performed up to the formation of a sandwich-type complex composed of an anti-PSA antibody, a GalNAc-PSA and a fluorescently-labeled GalNAc residue-affinity molecule and typically include, for example, the step of allowing a GalNAc-PSA 100 to bind to an anti-PSA antibody 64 and thereby capturing the GalNAc-PSA 100 in a measurement region 38 (capturing step) as shown in FIG. 1A, and the step of fluorescently labeling the GalNAc-PSA 100 by allowing a fluorescently-labeled GalNAc residue-affinity molecule 80 to bind thereto as shown in FIG. 1B (labeling step). Meanwhile, the steps of the measurement stage include, for example, the step of irradiating the back side of a metal thin film 14 with an incoming light and measuring the intensity of fluorescence emitted from the prescribed sandwich-type complex formed in the measurement region 38 (measurement step).

In SPFS, a plasmon excitation sensor 16a, which comprises: a dielectric member 12; the metal thin film 14 formed on the upper surface of the dielectric member 12; and the measurement region 38 formed on the surface of the metal thin film 14, is used. The measurement region 38 is where reactions for the formation of the prescribed sandwich-type complex are performed, and the measurement region 38 is preferably constituted by: a SAM 60 formed on the surface of the metal thin film 14; a support 62 bound to the surface of the SAM 60; and the anti-PSA antibody 64 bound to (carried on) the support 62. Such plasmon excitation sensor 16a is prepared in advance prior to the capturing step.

The SAM (Self-Assembled Monolayer) 60 is formed for the purpose of providing a scaffold for linking the support 62 on the surface side of the metal thin film 14 as well as for the purpose of inhibiting metal quenching, which is a phenomenon that the fluorescent substance 84, upon coming into contact with the metal thin film 14, stops emitting fluorescence even when irradiated with an excitation light. The SAM 60 is preferably formed from a silane coupling agent which has a functional group capable of directly or indirectly reacting with the metal thin film 14 and a functional group capable of directly or indirectly reacting with the molecules constituting the support 62 on the respective terminals.

The support 62 is formed for the purpose of incorporating the anti-PSA antibody 64 into the measurement region 38 at a higher density. That is, when the support 62 is bound to the SAM 60 and the anti-PSA antibody 64 is bound to the support 62, since the support 62 is spatially spread in the height direction, the number of the anti-PSA antibody 64 molecules per unit area (i.e., density) can be increased as compared to a case where the anti-PSA antibody 64 is directly bound to the SAM 60. Such support 62 is preferably made of a hydrophilic polymer which inhibits non-specific adsorption caused by hydrophobic bonding and has a large number of functional groups capable of reacting with the anti-PSA antibody 64, such as carboxymethyldextran (CMD) in which a large number of carboxyl groups are introduced to the main chain constituted by dextran.

For example, by bringing a solution containing 10-carboxy-1-decanethiol, which is a silane coupling agent, into contact with the surface of the metal thin film 14, the SAM 60 composed of the molecules thereof can be formed. Subsequently, after allowing the SAM 60 thus formed from 10-carboxy-1-decanethiol to react with N-hydroxysuccinimide (NHS) and water-soluble carbodiimide (WSC) and then active-esterifying the carboxyl groups oriented on the surface side of the SAM 60, a CMD-containing solution is brought into contact with the SAM 60, whereby the support 62 made of CMD can be immobilized. Further, CMD is allowed to react with NHS and WSC and the carboxyl groups of CMD are active-esterified, after which the resultant is brought into contact with a solution containing the anti-PSA antibody 64, whereby a large number of anti-PSA antibody 64 molecules can be carried on the support 62 made of CMD.

In the capturing step, a sample containing the GalNAc-PSA 100 and a non-GalNAc-PSA 110 is introduced to a flow channel 36 and thereby brought into contact with the measurement region 38. In the embodiment shown in FIG. 1, since the above-described fractionation using a lectin affinity column is not performed in advance, the sample contains the non-GalNAc-PSA 110 along with the GalNAc-PSA 100. Therefore, not only the GalNAc-PSA 100 but also the non-GalNAc-PSA 110 will be bound to and captured by the anti-PSA antibody 64 in the measurement region 38.

In the labeling step, a solution containing the fluorescently-labeled GalNAc-affinity molecule 80 is introduced to a flow channel 36 and thereby brought into contact with the measurement region 38. The fluorescently-labeled GalNAc-affinity molecule 80 binds to the GalNAc-PSA 10 captured in the measurement region 38 to form a prescribed sandwich-type complex; however, the fluorescently-labeled GalNAc-affinity molecule 80 does not bind to the non-GalNAc-PSA 110 having no GalNAc residue (except for inevitable binding through non-specific adsorption).

Between the capturing step and the labeling step and after the labeling step, it is preferred to introduce a washing liquid (e.g., a surfactant-containing buffer) to the flow channel 36 and thereby remove the non-GalNAc-PSA 110 and fluorescently-labeled GalNAc-affinity molecule 80 non-specifically adsorbing to the measurement region 38 (e.g., the support 62, the anti-PSA antibody 64 and the SAM 60). In the measurement step, it is preferred to measure the fluorescence intensity in a state where the flow channel 36 is filled with the washing liquid or a buffer.

SPFS System

Next, one embodiment of an SPFS system suitable for performing the above-described SPFS will be described referring to FIG. 2.

An SPFS system 1 is constituted by an SPFS measuring member 16, an SPFS measurement apparatus 10, and a control operation apparatus 40.

Figure 2A:
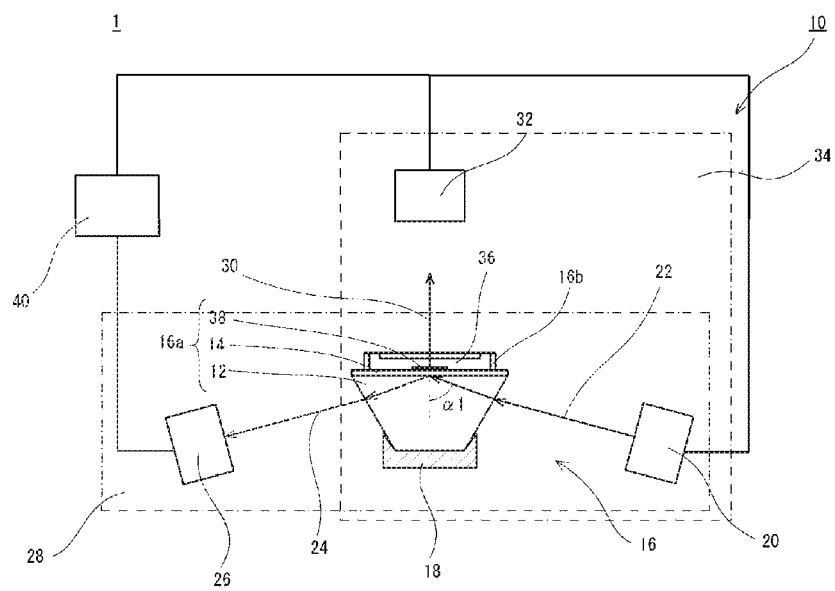
FIG. 2A illustrates an embodiment in which a metal thin film 14 is directly formed on an upper surface 12a of a dielectric member 12 and a plasmon excitation sensor 16a is constituted by the dielectric member 12, the metal thin film 14 and the measurement region 38.
Figure 2B:
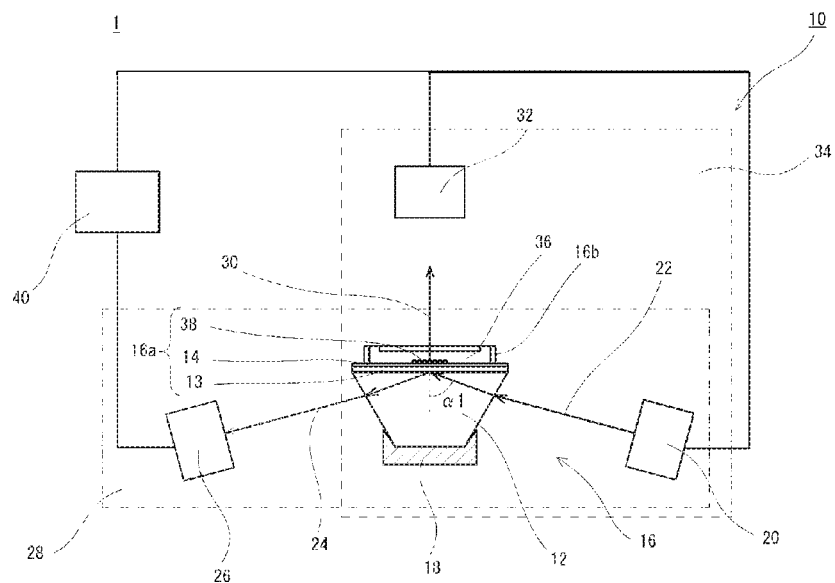
FIG. 2B illustrates an embodiment in which the metal thin film 14 is formed on the upper surface of a transparent planar substrate 13 that can be separated from the dielectric member 12 and the plasmon excitation sensor 16a is constituted by the transparent planar substrate 13, the metal thin film 14 and the measurement region 38.

FIG. 2A shows an embodiment in which the metal thin film 14 is directly formed on the upper surface 12a of the dielectric member 12, and a plasmon excitation sensor 16a is constituted by the dielectric member 12, the metal thin film 14 and the measurement region 38. FIG. 2B shows an embodiment in which the metal thin film 14 is formed on the upper surface of a transparent planar substrate 13 that can be separated from the dielectric member 12, and the plasmon excitation sensor 16a is constituted by the transparent planar substrate 13, the metal thin film 14 and the measurement region 38.

The SPFS measuring member 16 is constituted by the plasmon excitation sensor 16a and a flow channel member 16b. A region where a layer composed of the support 62 and the anti-PSA antibody 64 is formed on a part or the entirety of the upper surface of the plasmon excitation sensor 16a, that is, on a part or the entirety of the bottom surface of the flow channel 36, is the measurement region 38. The area of the measurement region 38 is usually adjusted to be equal to or larger than the irradiation area of an incoming light 22 which is generally irradiated as a laser light and, for example, when the spot diameter of the incoming light 22 is about 1 mmφ, the measurement region 38 usually has an area of at least several millimeters square.

The flow channel member 16b is a member for forming the flow channel 36, which has an opening at both ends, above the plasmon excitation sensor 16a, and is made of a colorless and transparent material such as polymethyl methacrylate (PMMA) so that the intensity of a fluorescence 32 can be accurately measured by a fluorescence detection means 32 arranged above the flow channel member 16b. The flow channel member 16b is press-bonded with the plasmon excitation sensor 16a (the dielectric member 12 in FIG. 2A or the transparent planar substrate 13 in FIG. 2B) and, if necessary, an adhesive, a matching oil, a transparent adhesive sheet or the like may be used to inhibit leakage of a solution from a gap therebetween. Further, the flow channel member 16b may be constituted by combining a side wall part (spacer) and a top plate part. In this case, as the side wall part, for example, a sheet-form member which is made of polydimethylsiloxane (PDMS) and has a through-hole serving as a flow channel on the center can be used. As the top plate part, for example, a plate-form member which is made of polymethyl methacrylate (PMMA) and thus colorless and transparent and has two through-holes at the positions corresponding to the respective ends of the through-hole (flow channel) of the side wall part can be used.

In such "flow channel-type" SPFS measuring member 16, various solutions such as a sample, a solution of the fluorescently-labeled GalNAc-affinity molecule 80 and a washing liquid are introduced to the flow channel 36 through the openings arranged at the respective ends thereof by a liquid transfer means (not shown) and are allowed to flow in a reciprocating or circulating manner.

When it is not necessary to transfer the solutions in a reciprocating or circulating manner, the SPFS measuring member 16 may be of a "well-type" in which the solutions are retained. In this case, a well member which can form a well having a larger volume than the flow channel on the upper surface of the plasmon excitation sensor 16a may be used in place of the flow channel member 16b. The upper part of the well may be open, and various liquids can be added to and removed from the well using, for example, a pipette-like equipment.

The SPFS measurement apparatus 10 basically comprises: a measuring member mounting section 18; an irradiation means 20; a light-receiving means 26; and a fluorescence detection means 32, and may further comprise a liquid transfer means (not shown) as required.

The SPFS measuring member 16 can be attached to and detached from the measuring member mounting section (stage) 18. When the use of such plasmon excitation sensor 16a comprising the dielectric member 12 as shown in FIG. 2A is postulated, the measuring member mounting section 18 is configured such that the prism-shaped dielectric member 12 can be set thereon. When the use of such plasmon excitation sensor 16a comprising the transparent planar substrate 13 as shown in FIG. 2B is postulated, the prism-shaped dielectric member 12 is set on the measuring member mounting section 18 in advance, and the transparent planar substrate 13 can be tightly mounted on the upper surface 12a of the dielectric member 12.

The liquid transfer means (not shown) can be constituted by, for example, a pipette-like equipment comprising a transfer means. Various solutions such as samples and reagents are each sucked up from a storing section (not shown) thereof, and the thus sucked solution is subsequently discharged through the opening arranged at one end of the flow channel 36 of the flow channel-type SPFS measuring member 16, whereby the solution can be introduced to the flow channel 36. As required, a reaction in the measurement region 38 can be facilitated by repeating the sucking and discharging operations on this spot to transfer a solution in the flow channel 36 in a reciprocating manner. When the SPFS measuring member 16 is of a well-type, a solution sucked into the well may be discharged. Further, when the SPFS measuring member 16 is of a flow channel-type, the liquid transfer means can also be constituted by an external flow channel and a pump. The external flow channel is a member which connects the openings arranged at the respective ends of the flow channel 36 of the SPFS measuring member 16 with the pump. The pump is capable of introducing various solutions, such as samples and reagents, into the flow channel 36 through this external flow channel and allowing the solutions to flow in a reciprocating or circulating manner.

The irradiation means 20 comprises a light source and a light source-moving means and may further comprise, as required, a polarization filter and a light attenuation filter between the light source and the dielectric member 12. The light source irradiates the incoming light 22 which has a wavelength and an intensity that are suitable for exciting the fluorescent substance 84 of the fluorescently-labeled lectin 80, and the light source is generally a laser diode (that is, the incoming light 22 is a laser light). The light source-moving means moves the light source in such a manner that the incoming light 22 is irradiated to the back side of the metal thin film 14 through a light entering-side surface 12b of the dielectric member 12 at a prescribed incidence angle α1. The polarization filter is used for P-polarization of the incoming light 22 irradiated from the light source so as to allow the metal thin film 14 to efficiently generate surface plasmon resonance. The light attenuation filter is used for adjusting the intensity (photon amount) of the incoming light 22 irradiated from the light source such that the fluorescence detection means 32 can acquire a signal value of an appropriate intensity.

The light-receiving means 26 comprises a light receiver and a light receiver-moving means. The light receiver receives a reflected light 24, which is the incoming light 22 reflected off the back side of the metal thin film 14, and is capable of measuring the intensity of the reflected light 24. The light receiver-moving means is capable of moving the light receiver in synchronization with changes in the incidence angle α1 of the incoming light 22 caused by the light source-moving means, such that the light receiver can surely receive the reflected light 24 with varying reflection angles. The most prominent electric field-enhancing effect attributed to surface plasmon resonance is attained when the ratio of the intensity of the reflected light 24 with respect to the intensity of the incoming light 22, namely the reflectance, is the lowest, and it is preferred to perform the measurement step of measuring the intensity of the fluorescence 32 at such an incidence angle α1.

The fluorescence detection means 32 comprises a detector, a condenser lens, and a filter. The detector is used for receiving the fluorescence 30 emitted from the surface of the plasmon excitation sensor 16a, that is, the fluorescence 30 emitted from the fluorescent substance 84 of the fluorescently-labeled lectin 80 captured in the measurement region 38, and measuring the intensity of the fluorescence 30 and, for example, a photomultiplier tube (PMT) can be used. The condenser lens is used for concentrating the fluorescence 30 to the detector and thereby enabling to accurately measure the intensity of the fluorescence 30 and, for example, an objective lens similar to that of a microscope can be used. The filter is used for allowing only a light that has a wavelength in a prescribed range including the fluorescence 30 to transmit therethrough and reach the detector, and the filter can remove any light that has a wavelength outside the prescribed range and causes a noise, such as scattering light.

It is noted here that the constitution composed of the SPFS measuring member 16 (plasmon excitation sensor 16a), the irradiation means 20 and the light-receiving means 26 may be referred to as "SPR measurement unit 28". The reason for this is because the SPR measurement unit 28 basically shares a common constitution with an apparatus for SPR method (surface plasmon resonance method) which quantifies a substance of interest not by measuring the fluorescence 30 but on the basis of attenuation of the intensity of the reflected light 24 caused by capturing of the substance of interest in the measurement region 38. Meanwhile, the constitution composed of the SPFS measuring member 16 (plasmon excitation sensor 16a), the irradiation means 20 and the fluorescence detection means 32 may be referred to as "SPFS measurement unit 34".

The control operation apparatus 40 is connected with the irradiation means 20, the light-receiving means 26, the fluorescence detection means 32 and the liquid transfer means (not shown) arranged as required, and transmits and receives signals such that the actions of the members of each means can be controlled and information measured by each means can be recorded, stored and calculated. The control operation apparatus 40 can be configured using a personal computer that is capable of storing programs and information for prescribed control operations.

The control operation apparatus 40 is capable of automatically operating the respective means in accordance with a program such that, for example, the liquid transfer means transfers solutions such as samples and reagents in prescribed amounts by a prescribed procedure to form a prescribed complex in the measurement region 38; the irradiation means 20 subsequently irradiates the incoming light 22 at a prescribed timing and a prescribed incidence angle; and the fluorescence detection means 32 measures the intensity of the fluorescence 30 generated in the measurement region 38. Further, the control operation apparatus 40 may be configured to receive and store data on the intensity of the fluorescence 30 measured for each sample from the fluorescence detection means 32 and, preferably, to immediately compare the thus measured values with a prescribed threshold value stored in advance and to further store the results of estimating the Gleason score.

[Estimation Method]

The threshold values for determining the Gleason score to be 7 or higher or to be 6 or lower based on a measured value of the GalNAc-PSA content (concentration) in a sample can each be set by a commonly used method in accordance with a threshold value for other diagnostic marker or tumor marker.

For example, when the GalNAc-PSA concentration is measured for samples derived from plural patients who have been definitively diagnosed with prostate cancer and tested for the Gleason score, a concentration at which the samples having an actual Gleason score of 7 or higher accounts for not less than a desired ratio in a group in which the thus measured value indicates a certain concentration or higher can be determined, and this concentration can be used as the threshold value for estimating that the Gleason score is 7 or higher. The above-described "desired ratio" corresponds to the reliability of estimation that the Gleason score is 7 or higher, that is, the probability of a correct estimation. The greater the number of the samples constituting a population of measurement data, the more reliable threshold value can be set. The measured value of the GalNAc-PSA content (concentration) in a sample is compared to the threshold value set in this manner, and the Gleason score of the prostate cancer patient from which the sample was collected can be estimated to be 7 or higher with a prescribed probability when the measured value is larger than the threshold value. It is desired that such a threshold value with which an estimation that the Gleason score is 7 or higher can be made with the highest possible accuracy; and that the Gleason score can thus be estimated (diagnosed) to be 7 or higher based on a measured concentration value which is larger than the threshold value without having to perform highly invasive needle biopsy.

In the same manner as described above, a concentration at which, when the GalNAc-PSA concentration is measured, the samples having an actual Gleason score of 6 or lower accounts for not less than a desired ratio in a group in which the thus measured value indicates a certain concentration or lower can be determined, and this concentration can be used as the threshold value for estimating that the Gleason score is 6 or lower. It is highly possible that the threshold value for estimating that the Gleason score is 7 or higher and the threshold value for estimating that the Gleason score is 6 or lower are different.

With regard to the above-described method of quantifying a glycoprotein having a sugar chain containing a specific sugar residue, such as GalNAc-PSA, particularly the quantification method based on an SPFS method, and the above-described method of obtaining specific information that can be used in diagnosis and the like where the thus quantified content is compared with a prescribed threshold value, reference can be made to, for example, WO 2010/090264 (Patent Document 4) and JP 2013-076666A (Patent Document 5) for general matters and variations of embodiments other than those described in the present specification.

EXAMPLES (1) Assembly of SPFS Measurement Apparatus

An SPFS measurement apparatus according to the embodiment illustrated in FIG. 2B was uniquely assembled and used in the below-described Examples. As the light source of the irradiation means 20, a laser diode (LD) capable of irradiating a light having a wavelength of 635 nm was used, and a light attenuation filter (neutral density filter) was arranged between the light source and the dielectric member 12 so that the photon amount could be adjusted. As the dielectric member 12, a prism of 60 degrees (manufactured by Sigmakoki Co., Ltd.) was used. On the upper surface 12a of this dielectric member 12, the measuring member 16 was constructed by immobilizing a member (sensor chip) constituted by the plasmon excitation sensor 16a comprising the transparent planar substrate 13 and the flow channel member 16b, which member was produced in the below-described manner. A photomultiplier tube (PMT) was used as a photodetector of the fluorescence detection means 32, and an objective lens was arranged as the condenser lens.

(2) Production of Flow Channel-Type SPFS Measuring Member

After plasma-cleaning a planar substrate made of glass having a refractive index of 1.72 and a thickness of 1 mm ("S-LAL 10", manufactured by Ohara Inc.), a chromium thin film was formed on one side of this substrate by sputtering. Then, a gold thin film was further formed on the surface of this chromium thin film by sputtering. The chromium thin film had a thickness of 1 to 3 nm, and the gold thin film had a thickness of 44 to 52 nm.

The substrate having the gold thin film formed in this manner was immersed in an ethanol solution containing 1 mM of 10-carboxy-1-decanethiol for at least 24 hours to form a SAM composed of the molecules on the surface of the gold thin film. The substrate was then removed from the solution and washed with ethanol and isopropanol, after which the substrate was dried using an air gun.

On this substrate, a 25 mM MES-buffered physiological saline, which contained 0.5 mM of N-hydroxysuccinimide (NHS), 0.5 mM of water-soluble carbodiimide (WSC) and 1 mg/mL of carboxymethyldextran (CMD) ("CMD-500-06I4", manufactured by Meito Sangyo Co., Ltd.: average molecular weight=500,000, degree of substitution=0.51), and a 10 mM NaCl solution (pH 6.0) were applied dropwise in an amount of 0.8 mL each and allowed to react for 20 minutes so as to bind CMD to SAM, whereby a CMD film was formed on the surface of the plasmon excitation sensor.

On this plasmon excitation sensor having the formed CMD film, a 0.5 mm-thick spacer made of polydimethylsiloxane (PDMS) having a through hole of 2 mm in width and 14 mm in length was arranged. A 2 mm-thick top plate made of polymethyl methacrylate (PMMA), which had through-holes at the positions corresponding to the respective ends of the through-hole of the spacer, was further arranged thereon. The plasmon excitation sensor, the spacer and the top plate were press-bonded and screw-fixed, whereby a flow channel-type SPFS measuring member comprising a flow channel constituted by the through-hole of the spacer through which samples, reagents and the like could be transferred via the through-hole of the top plate.

(3) Preparation of Antibody-Immobilized Substrate

[Preparation Example 1] Anti-PSA Monoclonal-Immobilized Substrate

An external flow channel and a peristaltic pump were connected to the produced flow channel-type SPFS measuring member, and ultrapure water and then phosphate buffered saline (PBS) were circulated for 10 minutes and 20 minutes, respectively, at room temperature (25° C.) and a flow rate of 500 μL/min, whereby the surface of the plasmon excitation sensor was equilibrated.

Subsequently, after circulating 5 mL of a phosphate buffered saline (PBS) containing 50 mM of N-hydroxysuccinimide (NHS) and 100 mM of water-soluble carbodiimide (WSC) for 20 minutes, 2.5 mL of an anti-PSA monoclonal antibody solution was circulated for 30 minutes so as to allow the antibody to bind to CMD, whereby an anti-PSA monoclonal antibody-immobilized CMD film (measurement region) was prepared.

Thereafter, by circulating a phosphate buffered saline (PBS) containing 1% by weight of bovine serum albumin (BSA) for 30 minutes, a non-specific adsorption-inhibiting treatment was performed in the flow channel.

(4) Production of Fluorescently Labeled Lectins

[Production Example 1] Alexa Fluor 647-Labeled WFA

The indicated fluorescently-labeled lectin was produced using a fluorescent substance labeling kit, "Alexa Fluor (registered trademark) 647 Protein Labeling Kit" (manufactured by Invitrogen Corp.). After mixing 100 μg-equivalent of WFA ("L-1350", manufactured by Vector Laboratories, Inc.) with 0.1 M sodium bicarbonate and an Alexa Fluor 647-reactive dye that are contained in the kit, and allowing them to react at room temperature for 1 hour, the resultant was subjected to gel filtration chromatography and ultrafiltration, whereby the Alexa Fluor 647-reactive dye that was not utilized for labeling was removed and a fluorescently-labeled WFA lectin was obtained. Then, the absorbance was measured to quantify the concentration of the indicated fluorescently-labeled lectin.

[Production Example 2] Alexa Fluor 647-Labeled SBA

The indicated fluorescently-labeled SBA was produced and the concentration thereof was quantified in the same manner as in Production Example 1, except that SBA ("L-1010", manufactured by Vector Laboratories, Inc.) was used in place of the WFA.

[Production Example 3] Alexa Fluor 647-Labeled VVL

The indicated fluorescently-labeled SBA was produced and the concentration thereof was quantified in the same manner as in Production Example 1, except that VVL ("L-1230", manufactured by Vector Laboratories, Inc.) was used in place of the WFA.

(5) Quantification of Prostate-Specific Antigen Having N-Acetylgalactosamine Residue at Sugar Chain Terminal (GalNAc-PSA) in Serum Sample

[Example 1] SPFS Measurement Using Alexa Fluor 647-Labeled WFA

Using the flow channel-type SPFS measuring member comprising the anti-PSA monoclonal antibody-immobilized substrate (Preparation Example 1) and the fluorescently-labeled WFA (Production Example 1), GalNAc-PSA contained in each test sample shown in Table 1 was quantified by SPFS. The details thereof were as follows.

100 μL of a dilution solution was added to 20 μL of each test sample (serum), and the resultant was thoroughly stirred in a test tube to prepare a mixed solution. This mixed solution in an amount of 100 μL was circulated in the flow channel and allowed to react with the measurement region for 60 minutes. The flow channel was subsequently washed for 3 minutes by TBS (TBS-T) containing 0.05% by weight of "Tween (registered trademark) 20". Next, 100 μL of the Alexa Fluor 647-labeled WFA solution obtained in Production Example 1 (WFA concentration: 10 μg/mL) was circulated in the flow channel to allow the solution to react with the measurement region for 10 minutes. Then, the flow channel was washed again for 5 minutes by the TBS-T. Thereafter, with the flow channel being filled with this TBS-T, an excitation light was irradiated thereto and the fluorescence intensity (signal) of Alexa Fluor 647 was measured by SPFS.

Figure 3:
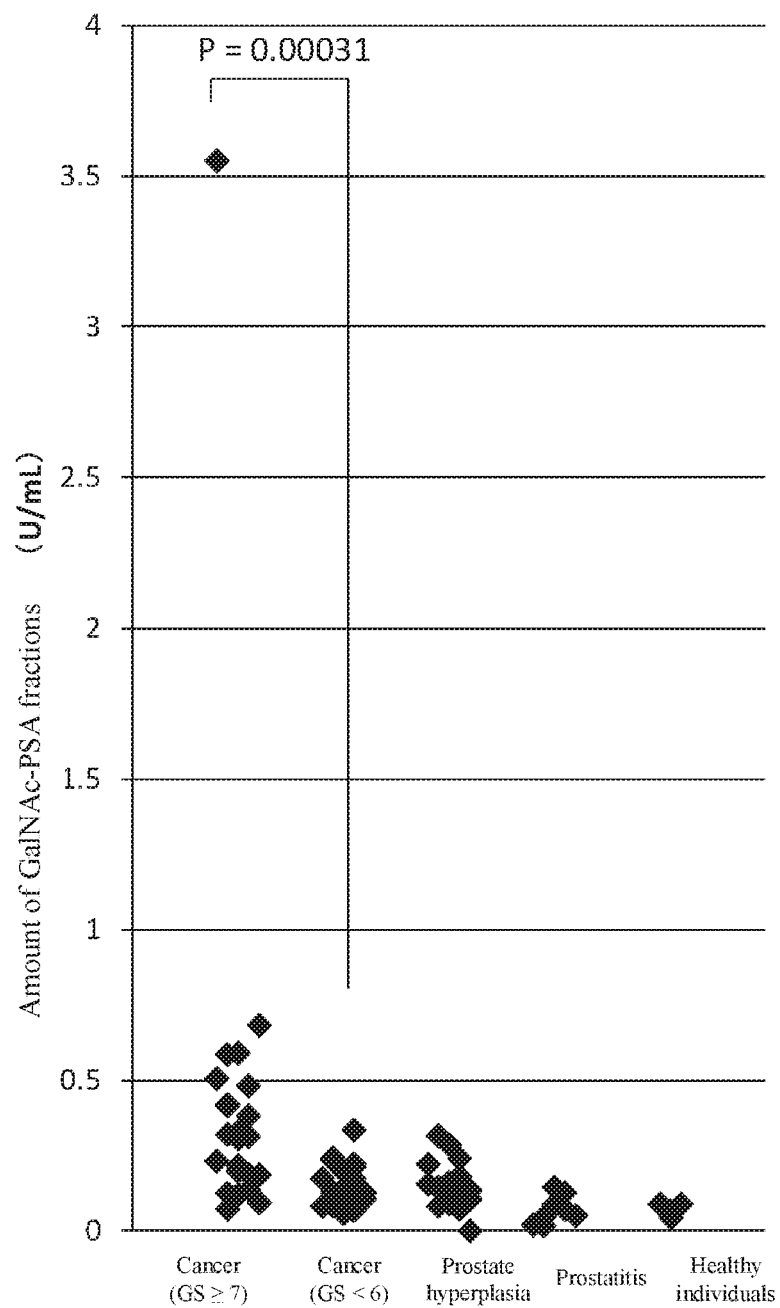
FIG. 3 is a graph showing the results of measuring the amount of GalNAc-PSA fractions contained in test samples in Example 1 (Alexa Fluor 647-labeled WFA) by SPFS. This graph is stratified based on the clinical information and the pathological tissue diagnosis results (Gleason scores) attached to the test samples shown in Table 1.

Based on the thus measured fluorescence intensity values of the each test samples and a calibration curve prepared from prepared samples having known concentrations, the GalNAc-PSA concentration (fraction amount) was calculated for each test sample. The results thereof are shown in FIG. 3. In those test samples derived from prostate cancer patients, it was revealed that there was a statistically significant difference (Mann-Whitney U-test, p=0.00031) between the group having a Gleason score (GS) of 7 or higher and the group having a Gleason score of lower than 6.

The cut-off values relating to the GalNAc-PSA concentration in the test samples and the correct estimation rate (prediction performance), which were set based on the above-described results for a Gleason score of 7 or higher and a Gleason score of 6 or lower are summarized in Table 2 and 3, respectively.

TABLE 2

| Cut-off value of GalNAc-PSA (U/mL) | Correct estimation rate for Gleason score of 7 or higher (prediction performance) |
|---|---|
| 0.33576 or higher | 100% |
| 0.24248 or higher | 93.3% |
| 0.13687 or higher | 70.0% |
| 0.08368 or higher | 60.0% |

TABLE 3

| Cut-off value of GalNAc-PSA (U/mL) | Correct estimation rate for Gleason score of 6 or lower (prediction performance) |
|---|---|
| less than 0.07303 | 100% |
| less than 0.12123 | 81.8% |
| less than 0.18671 | 75.0% |
| less than 0.30622 | 64.5% |

TABLE 1

| | Prostate cancer | | Benign disease | | Healthy individuals |
|---|---|---|---|---|---|
| | GS ≥7 | GS ≤6 | Prostatic hyperplasia | Prostatitis | |
| Number of cases | 25 | 21 | 20 | 8 | 4 |
| Gleason score (GS) breakdown | 7 (3 + 4): 16<br>7 (4 + 3): 6<br>8 (4 + 4): 2<br>9 (4 + 5): 1 | 6 (3 + 3): 21 | — | — | — |

[Example 2] SPFS Measurement Using Alexa Fluor 647-Labeled SBA

From the test samples shown in Table 1, a total of 8 samples consisting of 4 samples derived from prostate cancer patients having a Gleason score of 7 or higher and 4 samples derived from prostate cancer patients having a Gleason score of lower than 6 were randomly selected as measurement subjects. The fluorescence intensity (signal) of Alexa Fluor 647 was measured by SPFS and the GalNAc-PSA concentration (fraction amount) of each test sample was determined in the same manner as in Example 1, except that the Alexa Fluor 647-labeled SBA (SBA concentration: 10 µg/mL) obtained in Production Example 2 was used in place of the Alexa Fluor 647-labeled WFA solution (WFA concentration: 10 µg/mL).

Figure 4:
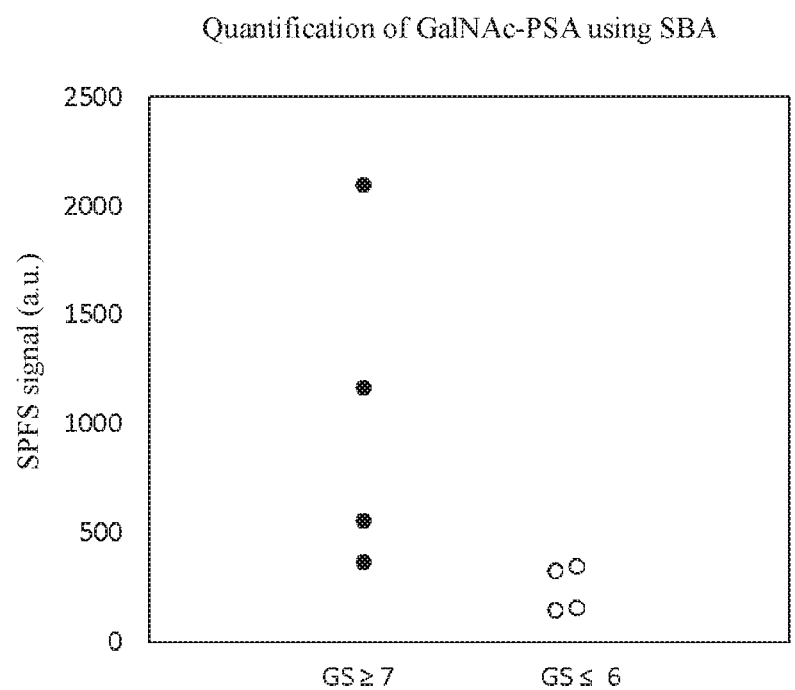
FIG. 4 is a graph showing the results of measuring the amount of GalNAc-PSA fractions contained in test samples in Example 2 (Alexa Fluor 647-labeled SBA) by SPFS. This graph is stratified based on whether the Gleason score is 7 or higher, or 6 or lower.

The results thereof are shown in FIG. 4. It was confirmed that the use of SBA as a lectin also shows the same tendency as the use of WFA (Mann-Whitney U-test, p=0.00428).

[Example 3] SPFS Measurement Using Alexa Fluor 647-Labeled VVL

From the test samples shown in Table 1, a total of 8 samples consisting of 4 samples derived from prostate cancer patients having a Gleason score of 7 or higher and 4 samples derived from prostate cancer patients having a Gleason score of lower than 6 were randomly selected as measurement subjects. The fluorescence intensity (signal) of Alexa Fluor 647 was measured by SPFS and the GalNAc-PSA concentration (fraction amount) of each test sample was determined in the same manner as in Example 1, except that the Alexa Fluor 647-labeled VVL (SBA concentration: 10 µg/mL) obtained in Production Example 3 was used in place of the Alexa Fluor 647-labeled WFA solution (WFA concentration: 10 µg/mL).

Figure 5:
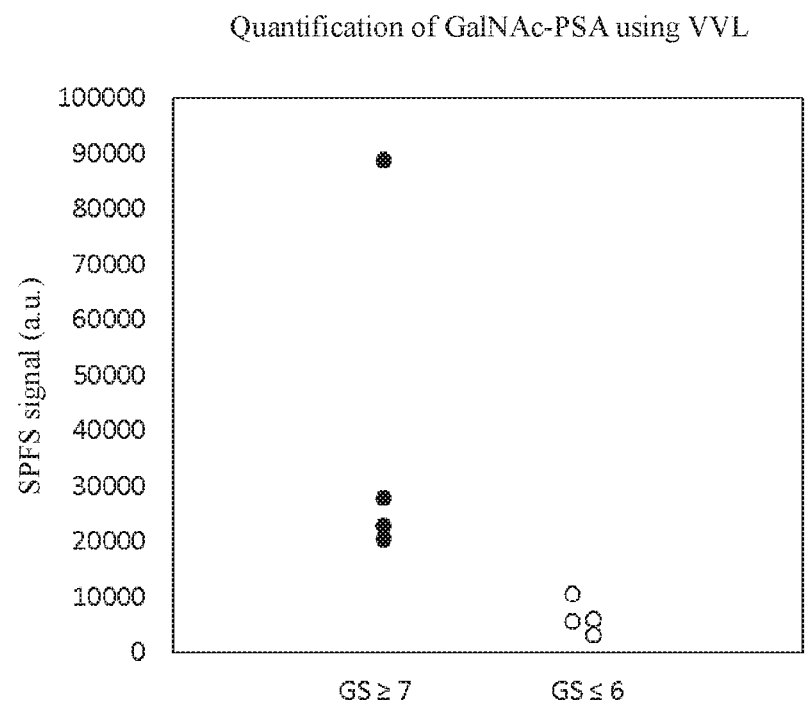
FIG. 5 is a graph showing the results of measuring the amount of GalNAc-PSA fractions contained in test samples in Example 3 (Alexa Fluor 647-labeled VVL) by SPFS. This graph is stratified based on whether the Gleason score is 7 or higher, or 6 or lower.

The results thereof are shown in FIG. 5. It was confirmed that the use of VVL as a lectin also shows the same tendency as the use of WFA (Mann-Whitney U-test, p=0.00141).

DESCRIPTION OF SYMBOLS

1: SPFS system
10: SPFS measurement apparatus
12: dielectric member
12a: upper surface
12b: light entering-side surface
12c: light reflecting-side surface
13: transparent planar substrate
14: metal thin film
16: SPFS measuring member (flow channel-type)
16a: plasmon excitation sensor
16b: flow channel member
18: measuring member mounting section
20: irradiation means
22: incoming light
24: reflected light
26: light-receiving means
28: SPR measurement unit
30: fluorescence
32: fluorescence detection means
34: SPFS measurement unit
36: flow channel
38: measurement region
40: control operation means
60: SAM
62: support
64: anti-PSA antibody
80: fluorescently-labeled GalNAc-affinity molecule
82: GalNAc-affinity molecule
84: fluorescent substance
100: GalNAc-PSA
102: PSA protein
104: sugar chain having GalNAc at a non-reducing terminal
104a: GalNAc
110: non-GalNAc-PSA
114: sugar chain having no GalNAc at a non-reducing terminal

The invention claimed is:

1. A method of determining a Gleason score that represents the malignancy of prostate cancer, said method comprising:
measuring the content of a prostate-specific antigen having an N-acetylgalactosamine residue at a non-reducing terminal of a sugar chain (GalNAc-PSA) in a sample;
comparing the measured content of GalNAc-PSA to a first threshold value for a Gleason score of 6 or lower, or comparing the measured content of GalNAc-PSA to a second threshold value for a Gleason score of 7 or higher; and
determining that the sample has a Gleason score of 7 or higher when the measured content of GalNAc-PSA is larger than the second threshold value, or determining that the sample has a Gleason score of 6 or lower when said measured content of GalNAc-PSA is smaller than the first threshold value,
wherein the measuring comprises binding to the GalNAc-PSA a molecule having affinity for β-N-acetylgalactosamine,
wherein said molecule having an affinity for a β-N-acetylgalactosamine residue is *Wisteria floribunda* lectin (WFA), soybean agglutinin (SBA), or *Vicia Villosa* lectin (VVL), and
wherein said PSA is quantified by surface plasmon-field enhanced fluorescence spectroscopy (SPFS).

2. The method according to claim 1, wherein the first threshold value and the second threshold value are the same.

3. The method according to claim 1, wherein the first threshold value and the second threshold value are different.

4. The method according to claim 1, wherein the first threshold value is derived from control samples having an actual Gleason score of 6 or lower and the second threshold value is derived from control samples having an actual Gleason score of 7 or higher.

* * * * *